USO05315995A

United States Patent [19]
Rivers

[11] Patent Number: 5,315,995
[45] Date of Patent: May 31, 1994

[54] METHOD AND APPARATUS FOR CONTINUOUS MEASUREMENT OF CENTRAL VENOUS OXYGEN SATURATION DURING HUMAN CARDIOPULMONARY RESUSCITATION AND CLINICAL SHOCK

[75] Inventor: Emanuel P. Rivers, Detroit, Mich.
[73] Assignee: Henry Ford Hospital, Detroit, Mich.
[21] Appl. No.: 853,926
[22] Filed: Mar. 19, 1992
[51] Int. Cl.$^5$ ............................................... A61B 5/00
[52] U.S. Cl. ..................................... 128/634; 356/41
[58] Field of Search ............... 128/633, 634, 673, 898, 128/632; 600/16–18; 356/39–41

[56] References Cited

U.S. PATENT DOCUMENTS

| 4,718,423 | 1/1988 | Willis et al. | 128/634 |
| 4,795,434 | 1/1989 | Kujawski | 604/159 |
| 5,048,524 | 9/1991 | Bailey | 128/634 |

OTHER PUBLICATIONS

M. B. Divertie et al., "Continuous Monitoring of Mixed Venous Oxygen Saturation" Chest Mar. 1984.
Averel B. Snyder et al., "Predicting short-term outcome of cardiopulmonary resuscitation using central venous oxygen tension measurements" Critical Care Medicine 1991.
Standards and guidelines for cardiopulmonary resuscitation (CPR) and emergency cardiac care (ECC). JAMA 1986; 225: 2905-2984.
Paradis N. A., Martin G. B., Rivers E. P., Goetting M. G., Appleton T. J., Feingold M. Nowak R. M.: Coronary perfusion pressure and the return of spontaneous circulation in human cardiopulmonary resuscitation. JAMA 1990; 263: 1106-1113.
Sanders A. B., Ewy G. A., Bragg S., Mathew A. Kern K. B.: Expired pCO2 as a prognostic indicator of successful resuscitation from cardiac arrest. Ann Emerg Med 1985; 14: 948-952.
Martin G. B., Gentile N. T., Paradis N. A., Moeggenber J., Appleton T. J., Nowak R. M.: Effect of Epinephrine on End-Tidal Carbon Dioxide Monitoring During CPR. Ann Emerg Med. 1990; 10: 396-398.
Callahan M., Barton C.: Effect of epinephrine administration on ability of end-tidal carbon dioxide readings to predict outcome of cardiac arrest. Ann Emerg Med 1990; 10: 4 (Abstract).
Weil M. H., Rackow E. C., Trevino R. Grundler W., Falk J. L., Griffel M. I.: Difference in acid-base state between venous and arterial blood during cardiopulmonary resuscitation. N Engl J Med 1986; 315: 153-156.
Capparelli E. V., Chow M. S. S., Kluger J., Feildman: Differences in systemic and myocardial blood acid-base status during cardiopulmonary resuscitation. Crit Care Med 1989; 17: 442-446.

(List continued on next page.)

Primary Examiner—Angela D. Sykes
Attorney, Agent, or Firm—Barnes, Kisselle, Raisch, Choate, Whittemore & Hulbert

[57] ABSTRACT

A fiber optic catheter for continuous measurement of central venous oxygen saturation (ScvO2) during human cardiopulmonary arrest and shock. When applied in cardiopulmonary arrest (cardiac arrest), the catheter provides therapeutic and prognostic guidelines in the management of a patient in this condition. The catheter also serves as a conduit for fluid and drug infusion and as a sampling port for venous blood. The catheter comprises a body having a first port that exits through a connector body to the computer interface that provides the sending signal and receiving signal which generates central venous oxygen saturation readings. A fiberoptic bundle of afferent and efferent light-conducting fibers transverses the first port to provide signal generation and interpretation of oxygen measured in the blood. A second port is a lumen that traverses and exits at the distal port to allow for pressure measurement and sampling of the venous blood. A third proximal port provides an opening of a lumen that transverses and exits the catheter via a side port spaced from the skin insertion site.

11 Claims, 1 Drawing Sheet

OTHER PUBLICATIONS

Adrogue H. J., Rashad N., Gorin A. B., Yacoub J., Madias N. E.: Assessing acid-base status in circulatory failure. N Engl J. Med 1989; 320: 1312-1316.

Nowak R. M., Martin G. B., Carden D. L., Tomlanovich M. C. Selective venous hypercarbia during human cpr: Implications regarding blood flow. Ann Emerg Med 1987; 16: 527-530.

Rivers E. P., Paradis N. A., Martin G. B. Goetting M. G., Rosenburg J., Appliton, Nowak R. M.: Systemic oxygen extraction during prolonged CPR in humans. Crit Care Med 1989; 17-S72 (Abstract).

Snyder A. B., Salloum L. J., Barone J. E., Conley M., Todd M., Digiacomo: Predicting short-term outcome of cardiopulmonary resuscitation using central venous oxygen tension measurement. Crit Care Med 1991; 19: 111-113.

Scalea T. M., Hartnett R. W., Duncan A. O., Atweh N. A., Phillips T. F., Sclafani S. J., Fuortes M., Shaftan G. W.: Central venous oxygen saturation: a useful tool in trauma patients. J Trauma 1990; 30: 1539-1543.

Kazarian K. K., Del Guercio L. R. M.: The use of mixed venous blood gas determinations in traumatic shock. Ann Emerg Med 1980; 9: 179-182.

Kandel G., Aberman A.: Mixed venous oxygen saturation–its role in the assessment of the critically ill patient. Arch Intern Med 1983; 143: 1400-1402.

Tahvananinen J., Meretoja O., Nikki P.: Can central venous blood replace mixed venous blood samples? Crit Care Med 1982; 10: 758-761.

Lee J. F., Wright R., Barber R., Stanley L.: Central Venous oxygen saturation in shock-a study in man. Anesthesiology 1971; 36(5): 472-470.

Scheinman M. M., Brown M. A., Rapaport E.: Critical assessment of use of central venous oxygen saturation as a mirror of mixed venous oxygen in severely ill cardiac patients. Circulation XL 1969; 165-172.

Goldman R. H., Klughhaupt M., Metcalf T., Spivack A. P., Harrison D. C. Measurement of central venous oxygen saturation in patients with myocardial infraction. Circulation. 1968; XXXVIII: 941-947.

Emerman C. L., Pinchak A. C., Hagen J. F., Hancock D.: A comparison of venous blood gases during cardiac arrest. Am J Emerg Med 1988; 6: 580-583.

Divertie M. B., McMichan J. C.: Continous monitoring of mixed venous oxygen saturation. 1984 Chest 85; 3: 423-428.

Martin G. B., Rivers E. P., Paradis N. A., Goetting M. G., Appleton T. J., Nowak R. M.: Systemic oxygen utilization during cardiopulmonary bypass in cardiac arrest patients. Crit Care Med 1990; 18: S276 (Abstract).

Miller M. J.: Tissue oxygenation in clinical medicine–an historical review. Anesth & Anal 1982 6; 61: 527-535.

Del Guercio L. R. M., Coomaraswamy R. P., State D.: Cardiac output and other hemodynamic variables during external cardiac massage in man. N Engl J Med 1963; 269: 1398-1404.

Kasnitz P., Druger G. L., Yorra, Simmons D. H.: Mixed venous oxygen tension and hyperlactemia. JAMA 1976; 236: 570-574.

Miller M., Cook W., Mithoefer J.: Limitations of the use of mixed venous pO2 as an indicator of tissue hypoxia. Clin Res 1979; 27:401A.

Lewinter J. R., Carden D. L., Nowak R. M., Enriquez E. Martin G. B. CPR-dependent consciousness: evidence for cardiac compression causing forward flow. Ann Emerg Med 1989; 1-8: 1111-1115.

Krouskop R. W., Cabatu E. E., Bhaktharaj C. P., McDonnell F. E., Brown E. G.: Accuracy and clinical utility of an oxygen saturation catheter. Crit Care Med 1984; 11: 744-749.

Birman H., Haq A., Hew E., Aberman: Continuous monitoring of mixed venous oxygen saturation in hemodynamically unstable patients. Chest 1984; 86: 753-756.

Baele P. L., McMichan J. C., Marsh H. M., Sill J. C., Southorn P. A.: Continuous monitoring of mixed venous oxygen saturation in critically ill patients. Anesth Analg 1982; 61: 513-517.

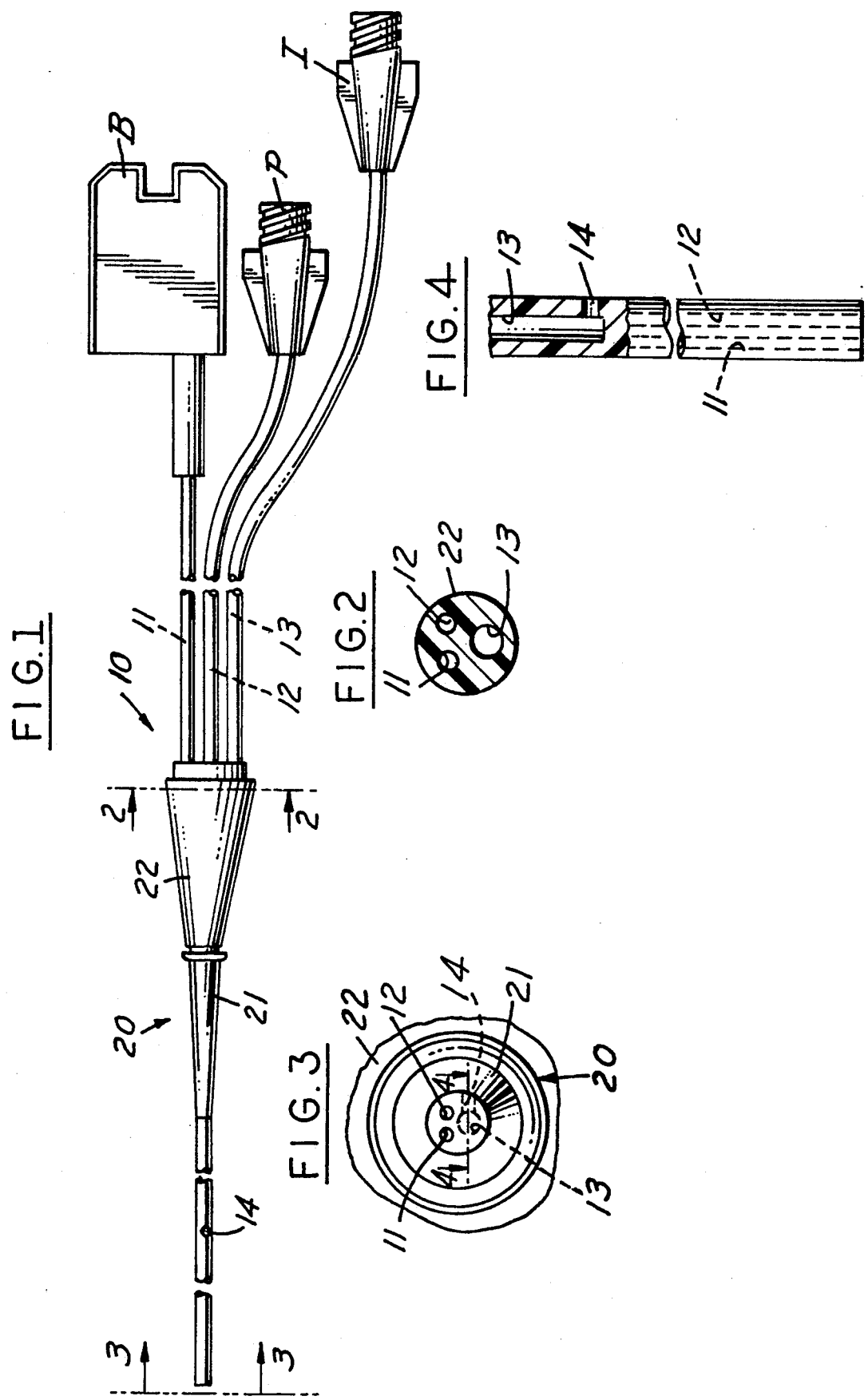

METHOD AND APPARATUS FOR CONTINUOUS MEASUREMENT OF CENTRAL VENOUS OXYGEN SATURATION DURING HUMAN CARDIOPULMONARY RESUSCITATION AND CLINICAL SHOCK

This invention relates to a method and apparatus for measuring central venous oxygen saturation and treatment during human cardiopulmonary resuscitation (cardiac arrest) and clinical shock.

BACKGROUND OF THE INVENTION

Cardiac arrest is one of the most dynamic pathophysiologic events in clinical medicine. An immediate cascade of pathologic processes is triggered secondary to the abrupt cessation of oxygen delivery. Since oxygen is not stored in sufficient quantities in the body, interruption of adequate oxygen transport to the cells for brief periods of time can result in death. Advanced cardiac life support (ACLS) attempts to provide oxygen delivery ad thereby attenuate this cascade. Rapid and substantial improvement in oxygen delivery is required to decrease the morbidity and mortality of ischemic organ injury. Current monitoring techniques used in ACLS include continuous electrocardiographic monitoring and physical examination e.g. palpation of the carotid or femoral pulse. Both of these techniques provide little information regarding hemodynamic status and oxygen delivery to the brain or body.

Clinical monitoring techniques used as prognostic and therapeutic indicators during ACLS include the coronary perfusion pressure (CPP) or aortic to right atrial relaxation phase pressure gradients, and end-tidal carbon dioxide concentration (ETC02). The importance of CPP as a prognostic indicator of return of spontaneous circulation (ROSC) during animal and human CPR is well established. CPP is the "gold" standard for measuring hemodynamic response to therapy during CPR. Calculation of CPP requires placement of both an aortic artery and central venous catheter which may limit its applicability. ETC02 has been studied in animals and humans and has been proposed as a prognostic and therapeutic guide during CPR. Although ETC02 has the advantage of being non-invasive, it is influenced by multiple variables (i.e. aspiration, pre-existing pulmonary disease) that may limit its reflection of blood flow and CPP in the setting of cardiac arrest. ScvO2 monitoring in accordance with the present invention requires only central venous cannulation while Ao-Ra requires venous and arterial cannulation. ScvO2 monitoring is not affected by the same extrinsic variables that affect ETC02.

Mixed venous blood reflects tissue oxygen (02) delivery during cardiac arrest-and-circulatory failure. Selective venous hypoxemia or low oxygen content when compared to arterial blood are characteristic during cardiac arrest. Intermittent mixed venous oxygen saturation measurement during ACLS predicts outcome in cardiac arrest patients and hemodynamically unstable trauma patients. In studies made in accordance with the invention, patients successfully resuscitated had higher central venous oxygen saturations than non-resuscitated patients. As far as the present invention is aware, this is the first measurement of this parameter continuously in cardiac arrest patients with fiberoptic technology.

Ideally, mixed venous blood should be drawn from a pulmonary artery catheter. However, placement of such a catheter is unlikely during cardiac arrest. A number of studies have supported the substitution of central venous (right arterial or superior vena cava) blood for mixed venous blood (pulmonary arterial) during spontaneous circulation, circulatory failure and closed chest ACLS. There is reported no significant difference between pulmonary artery, central and femoral venous blood gases during closed chest ACLS in animals.

The catheter in accordance with the invention and methods using the catheter utilize the concept of ScvO2. The information provided by such a catheter is a guide to the care of patients in cardiac arrest. It is believed that this is the first utilization of a catheter of this type in this clinical situation. The present invention includes a catheter and methods specific for utilization in cardiopulmonary resuscitation.

SUMMARY OF THE INVENTION AND METHOD

It is an object of this invention to provide a catheter and method of utilizing continuous central venous oxygen measurement during cardiac arrest. This will enable a treating clinician to tailor therapy and formulate a prognosis in the treatment of a patient in shock and cardiac arrest. Using the concentration of oxygen in central venous blood, decisions can be made regarding hemodynamic status in response to therapy and predict outcome.

In accordance with the invention, a fiberoptic catheter is provided for continuous measurement of central venous oxygen saturation (ScvO2) during human cardiopulmonary arrest and shock. When applied in cardiopulmonary arrest, the catheter provides therapeutic and prognostic guidelines in the management of a patient in this condition. The catheter also serves as a conduit for fluid infusion, drug administration, and as a sampling port for venous blood. The catheter comprises a body having a first port that exits through a connector body to the computer interface and provides the sending signal and receiving signal that generates central venous oxygen saturation readings. A fiberoptic bundle of afferent and efferent light-conducting fiber transverses the first port to provide signal generation and interpretation of oxygen measured in the blood. A second port is a lumen that traverses and exits at the distal port to allow for pressure measurement and sampling of the venous blood. A third proximal port provides an opening of a lumen that transverses and exits the catheter via a side port 10 cm from the skin insertion site.

DESCRIPTION OF THE DRAWINGS

FIG. 1 is a schematic of a fiber optic catheter embodying the invention and adapted to be used in the method.

FIG. 2 is a sectional view taken along the line 2—2 in FIG. 1.

FIG. 3 is a sectional view taken along the line 3—3 in FIG. 1.

FIG. 4 is an end view from the left as viewed in FIG. 1.

DESCRIPTION

In accordance with the invention, the method and apparatus for measuring central venous oxygen saturation comprises a fiber optic catheter 10 for continuous measurement of central venous oxygen saturation (ScvO2) during human cardiopulmonary arrest and shock. When applied in cardiopulmonary arrest, the catheter provides therapeutic and prognostic guidelines in the management of a patient in this condition. The catheter also serves as a conduit for fluid and drug infusion and as a sampling port for venous blood. The catheter comprises a body 10 having a first port 11 that exits through the connector body B to the computer interface and provides the sending signal and receiving signal that generates central venous oxygen saturation readings. A fiberoptic bundle of afferent and efferent light-conducting fibers transverses the first port 11 (diameter 0.6 mm) to provide signal generation and interpretation of oxygen measured in the blood. A second port 12 is a lumen that traverses and exits at the distal port P to allow for pressure measurement and sampling of the venous blood. A third proximal 13 port provides an opening of the lumen from proximal infusion port I that transverses and exits the catheter via a side port 14 preferably less than 10 centimeters from the skin insertion site. These ports allow for pressure measurement, fluid or drug administration. The placement of port 14 is important to avoid signal artifact (distortion) when infusing large volumes of fluid or drugs.

Referring to FIGS. 1 and 2, the catheter 10 includes a body 20 including a first catheter portion 21 and a second frustoconical body portion 22. The first portion 21 is adapted to be inserted into the blood vessel and preferably has a length of at least 19 cm. The first portion 21 is capable of flexing during insertion but has sufficient rigidity that it will not be flexed during turbulent blood flow. The body 20 further includes a second portion 22 that is sufficiently rigid to maintain the lumens relatively fixed to one another and to withstand the external compression forces of an introducer of conventional construction. The lumens 11, 12, 13 extend externally from body 20 to the respective connector body B, distal port P and proximal infusion port I.

Referring to FIGS. 1 and 2, a preferred form of the catheter 10 comprises a body of urethane having three lumens extending therethrough. The polyurethane catheter may have a length of 19 centimeters long and a diameter of 7 French for optimal placement into the (patient) venous system. The 7 French diameter is needed for the appropriate compliance. It has a slight curvature to avoid contact with the vessel walls as it enters and resides in the venous system. It can be placed through an introducer, preferably 7.5 French, to avoid damage to the optic fibers that exit from the distal port. The proximal or first portion 21 aspect of the catheter as it enters the skin is reinforced and tapered for 3 centimeters to avoid damage of the fiberoptic bundles and compression of the infusion and sampling ports when a tight fitting introducer is used.

The proximal aspect of the catheter 10 has a first port 11 that exits through a connector body to the computer interface and provides the sending signal and receiving signal that generates central venous oxygen saturation readings. A fiberoptic bundle of afferent and efferent light-conducting fiver transverses the first port 11 (diameter 0.6 mm) to provide signal generation and interpretation of oxygen measured in the blood. A second port 12 is a lumen that traverses all 19 centimeters (0.6 mm) and exits at the distal port to allow for pressure measurement and sampling of the venous blood. A third proximal port 13 (0.9 mm) provides an opening of the lumen that transverses and exits the catheter via a side port 10 centimeters from the skin insertion site.

In a study approved by the Henry Ford Hospital Institutional Review Board for Human Research, one hundred consecutive patients presented to the emergency department (ED) in non-traumatic, normothermic cardiopulmonary arrest were studied. Cardiopulmonary arrest was defined as the absence of a palpable pulse and respirations and was later verified by the absence of spontaneous aortic pulsations on the pressure tracing. Patients received only basic Cardiac Life Support (BCLS) by emergency medical service (EMS) personnel prior to admittance to the ED. Upon arrival, patients were clinically managed by emergency medicine physicians using Advanced Cardiac Life Support (ACLS) guidelines. The epinephrine dose (0.01 to 0.2 mg/kg) was used at the clinician's discretion. CPR was performed by a pneumatic compression device (Thumper, Michigan Instruments, Grand Rapids, Mich.) at a compression rate of 80/minute and an excursion of 1½-2 inches. Ventilation of 80% oxygen was provided between compressions at a 5:1 ratio. Catheter placement, data recording and blood sampling were performed by on-call research personnel, who had no active involvement in the clinical management of the patient.

All catheters were simultaneously placed. A 7.5 French introducer was percutaneously placed into the central venous system via the subclabian vein. "French" is a customary unit of measure for catheter and needle diameter, one French being equal to a third of a millimeter. The side port 14 was used for drug and fluid administration. The infrared, fiberoptic catheter 10 was advanced through the central port of the introducer into the central venous system. The distal lumen 12 on the fiberoptic catheter was used for central venous gas sampling and pressure measurement.

For arterial pressure monitoring, a 60 cm 5.8 French catheter was placed in the aortic arch, either percutaneously or by cut down technique, via the femoral artery. The catheters were connected to precalibrated pressure transducers through a heparinized saline flush system. The resulting signals were amplified and pressure tracings were recorded throughout CPR and during the initial post-resuscitation period. Correct catheter positions were confirmed by supine chest radiograph at the end of ACLS.

Hemoglobin, hematocrit, simultaneous arterial and venous blood gases were obtained every 10 minutes throughout the resuscitation. The fiberoptic catheter 10 was precalibrated in vitro before insertion. During the cardiac arrest, the initially measured 02 saturation of the venous blood gas samples was used for an in vivo calibration of the ScvO2 monitor. Initial (the first values obtained in the arrest), mean (average of all values obtained during arrest) and maximal (higher value obtained during the cardiac arrest before return of spontaneous circulation (ROSC) were recorded.

ROSC was defined as the development of a spontaneous pulse wave form on the arterial tracing associated with a systolic blood pressure greater than 60 mm Hg for more than 5 minutes. Cardiac arrest was defined as the absence of a pulsatile arterial tracing or a systolic blood pressure of less than 60 mm Hg.

Sixty-eight episodes of ROSC or blood pressure were observed. Patients with ROSC had higher initial, mean, and maximal ScvO2 compared to those without ROSC ($p=0.23, 0.0001$, and $0.0001$, respectively). The positive predictive value for ROSC with a maximum ScvO2 of greater than 60% and 72% was 0.93 and 1.0, respectively. The negative predictive value for ROSC with a maximum ScvO2 of less than 30% and 40% was 1.0 and 0.93 respectively. Only one of 68 episodes of ROSC was attained with a maximum ScvO2 of less than 40%. High dose epinephrine (0.2 mg/kg) depresses ScvO2 temporarily, and this effect decreases with the duration of arrest. Continuous ScvO2 monitoring can serve as an adjunct in monitoring therapeutic response and as an prognosticator of ROSC during cardiopulmonary resuscitation (CPR).

Using the catheter of this invention and data obtained, one can determine the effectiveness of therapy in providing adequate circulation or blood flow during CPR. This is the amount of oxygen that is delivered throughout the body. When the ScvO2 is above 60%, the chances of having a blood pressure or beating heart is 93%. When the ScvO2 is above 72%, there is a 100% chance of having a blood pressure. If the patient never obtains an ScvO2 of above 40%, there is no chance of survival and should not be resuscitated indefinitely beyond 30 minutes with a value below this number.

The catheter thus provides the following advantages:

1. A fiber optic central venous catheter and methods specifically for use in cardiopulmonary resuscitation and shock.

2. A fiber optic catheter specific for use in the central venous position during cardiac arrest and shock states in which the patient is resuscitated from low or no blood pressures. In this condition the patient is in delivery dependent oxygen consumption state which allows for the use of ScvO2 as a diagnostic and therapeutic modality. It has greater prognostic value than measurement of arterial blood pressure.

Thus, in accordance with the invention, the catheter comprises
   three lumens,
   a body,
   said body having a first portion that extends into the blood vessel for a length of at least 19 cm,
   said first portion being capable of flexing during insertion but will remain rigid and not flex during turbulent blood flow,
   a second portion being rigid to maintain the lumens relatively fixed to one another and to withstand the external compression forces of an introducer,
   said lumens extending externally to a connector body to a computer interface, a distal infusion port and a proximal infusion port, respectively,
   said lumens for said proximal infusion port extending radially to a side surface of the first portion of the body.

The length of the catheter portion 21 is preferably less than 20 cm from the skin to the end of the catheter. The lumen side port 14 must be at least 9 cm from the end of the catheter portion 21 and must be flexible to avoid contact with the blood vessel walls and must be sufficiently rigid that it will not flex due to variations in blood pressure.

The method of managing a patient in cardiac arrest who is undergoing CPR comprises
   placing first portion of a catheter in the central venous system,
   connecting one lumen to computer to measure central venous oxygen saturation,
   utilizing said second and third lumens for volume and fluid infusion, pressure measurement and sampling of venous blood in accordance with ACLS guidelines.

In accordance with the invention:
   (a) if ScvO2 is greater than 60%, interrupting the CPR and obtaining the blood pressure such that advanced cardiac life support can be tailored to treating a spontaneously beating heart,
   (b) if the ScvO2 is above 73%, interrupting CPR and treating the patient as one with a spontaneously beating heart,
   (c) if the patient does not attain an ScvO2 of above 40% during 30 minutes of recording and treatment for cardiac arrest, continued attempts at resuscitation are not warranted.

I claim:

1. A central venous oxygen saturation catheter for use in treating a patient for human cardiopulmonary resuscitation and shock during and after cardiac arrest comprising:
   a body,
   a first lumen traversed by a fiber optic bundle of afferent and efferent light-conducting fiber means for sending signals and receiving signals for generating central venous oxygen saturation readings,
   said body having a first portion which has a distal end and a diameter enabling insertion into a central venous blood vessel,
   said body having a substantially frustoconical second portion adjacent said first portion,
   said first portion being capable of flexing during insertion but remaining sufficiently rigid and not flexing during turbulent blood flow,
   said first portion of said catheter body having a length that is less than 19 cm.

2. The central venous oxygen saturation catheter set forth in claim 1 including a connector means connected to said first lumen for attachment to a fiber optic computer interface.

3. The central venous oxygen saturation catheter set forth in any one of claims 1 and 2 including a second lumen extending to a distal port to allow for pressure measurement and sampling of venous blood.

4. The central venous oxygen saturation catheter set forth in claim 3 including a third lumen having a proximal infusion port for fluid or drug administration.

5. The central venous oxygen saturation catheter set forth in claim 4 wherein said proximal infusion port is at least 10 cm from said distal end of said first portion of the catheter.

6. The method of managing a patient for, during and after cardiac arrest and shock which comprises:
   providing a fiber optic catheter,
   inserting said catheter into a central venous blood vessel to a distance less than 19 cm,
   connecting said catheter to a fiber optic computer interface, and
   continuously measuring the central venous oxygen saturation (ScvO2) during and after cardiopulmonary arrest and shock.

7. The method set forth in claim 6 wherein said step of providing a fiber optic catheter includes forming a body having said first lumen in said body,
   said body having a first portion that is inserted to extend into a venous blood vessel to a length of less than 19 cm, said first portion having a distal end,
   said first portion being capable of flexing during insertion but remaining rigid and not flexing during turbulent blood flow,
   said body having a second portion which is rigid.

8. The method set forth in any one of claims 6-7 including the steps of
   (a) if the ScvO2 is greater than 60% during CPR, interrupting CPR and obtaining the blood pressure such that advanced cardiac life support (ACLS) can be tailored to a beating heart, (b) if the ScvO2 is above 73%, immediately interrupting CPR and treating the patient as one with a beating heart, (c) if the patient does not attain an ScvO2 of above 40% during 30 minutes of recording and treatment for cardiac arrest, discontinuing further attempts at resuscitation, (d) if the ScvO2 is less than 40% after a heart beat is established taking precautions immediately because the patient will have another cardiac arrest within minutes.

9. The method set forth in claim 8 including the step of providing a second lumen extending to the end of the catheter to allow for pressure measurement and sampling of venous blood and monitoring pressure and sampling venous blood through said second lumen.

10. The method set forth in claim 9 including the step of providing a third lumen having a proximal infusion port for fluid or drug administration, said proximal infusion port extending radially to a side surface of the first portion of the body and administering fluid and drugs through said third lumen as required.

11. The method set forth in claim 10 including the step of providing said proximal infusion port such that said port is less than 19 cm from the end of the distal tip of the catheter.

* * * * *